US010213348B2

(12) United States Patent
Gualtieri et al.

(10) Patent No.: US 10,213,348 B2
(45) Date of Patent: Feb. 26, 2019

(54) ELASTIC STRUCTURE FOR ABSORBENT SANITARY PRODUCTS, AND A METHOD AND APPARATUS FOR ITS PRODUCTION

(71) Applicant: Fameccanica.Data S.p.A., Pescara (IT)

(72) Inventors: Diego Gualtieri, Pescara (IT); Serafino Lupinetti, Elice (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 399 days.

(21) Appl. No.: 15/014,683

(22) Filed: Feb. 3, 2016

(65) Prior Publication Data
US 2016/0228305 A1    Aug. 11, 2016

(30) Foreign Application Priority Data

Feb. 11, 2015    (IT) .......................... 102015000005899

(51) Int. Cl.
*A61F 13/49* (2006.01)
*A61F 13/15* (2006.01)
(Continued)

(52) U.S. Cl.
CPC .. *A61F 13/49009* (2013.01); *A61F 13/15593* (2013.01); *A61F 13/15739* (2013.01);
(Continued)

(58) Field of Classification Search
CPC .......... A61F 13/49009; A61F 13/49011; A61F 13/15593; A61F 13/15739; A61F 13/4902;
(Continued)

(56) References Cited

U.S. PATENT DOCUMENTS 6,291,039 B1 * 9/2001 Combe ................ A41D 27/245
428/35.2
7,582,348 B2    9/2009 Ando et al.
(Continued)

FOREIGN PATENT DOCUMENTS

EP    0886480    12/1998
EP    1876275    1/2008
(Continued)

OTHER PUBLICATIONS

Italian Search Report and Written Opinion dated Nov. 9, 2015 for Application No. 102015000005899.

*Primary Examiner* — Philip R Wiest
(74) *Attorney, Agent, or Firm* — Patterson & Sheridan, LLP

(57) ABSTRACT

An elastic structure for absorbent sanitary products, comprising a sleeve comprising a first layer and a second layer overlapping each other, at least one elastic thread, and a plurality of first connecting portions spaced apart in a longitudinal direction, wherein each of said first connecting portions comprises two first welds arranged on opposite sides of the thread, wherein the first welds weld said first and second layers to each other in a first longitudinal portion of said sleeve, and a plurality of second connecting portions spaced apart in the longitudinal direction, wherein each of said second connecting portions comprises at least one second weld, wherein said second welds weld said first and second layers to each other in a second longitudinal portion of said sleeve without axially connecting the thread to said second longitudinal portion of the sleeve.

13 Claims, 3 Drawing Sheets

(51) Int. Cl.
  B29C 65/08 (2006.01)
  B29C 65/00 (2006.01)
  B29L 31/48 (2006.01)
  B29C 65/18 (2006.01)

(52) U.S. Cl.
  CPC ........ A61F 13/4902 (2013.01); B29C 65/087 (2013.01); B29C 66/135 (2013.01); B29C 66/21 (2013.01); B29C 66/232 (2013.01); B29C 66/4332 (2013.01); B29C 66/81429 (2013.01); B29C 66/83411 (2013.01); B29C 66/83511 (2013.01); *A61F 2013/49025* (2013.01); *A61F 2013/49031* (2013.01); *B29C 65/18* (2013.01); *B29C 66/71* (2013.01); *B29C 66/7294* (2013.01); *B29L 2031/4878* (2013.01)

(58) Field of Classification Search
  CPC . A61F 2013/49025; A61F 2013/49031; B29C 65/087; B29C 66/135; B29C 66/21; B29C 66/232; B29C 66/4332; B29C 66/81429
  See application file for complete search history.

(56) References Cited

U.S. PATENT DOCUMENTS

| | | |
|---|---|---|
| 2006/0069373 A1 | 3/2006 | Schlinz et al. |
| 2006/0270302 A1 | 11/2006 | Ando et al. |
| 2010/0076394 A1 | 3/2010 | Hayase et al. |
| 2012/0095429 A1 | 4/2012 | Kobayashi et al. |
| 2013/0306226 A1 | 11/2013 | Zink et al. |
| 2016/0228305 A1 | 8/2016 | Gualtieri et al. |

FOREIGN PATENT DOCUMENTS

| | | |
|---|---|---|
| EP | 2186493 | 5/2010 |
| WO | 2009067055 A1 | 5/2009 |
| WO | 2010126415 | 11/2010 |

\* cited by examiner

ELASTIC STRUCTURE FOR ABSORBENT SANITARY PRODUCTS, AND A METHOD AND APPARATUS FOR ITS PRODUCTION

CROSS-REFERENCE TO RELATED APPLICATIONS

This application claims benefit of Italian patent application number 102015000005899, filed Feb. 11, 2015, which is herein incorporated by reference.

BACKGROUND OF THE INVENTION

Field of the Invention

The present invention relates to an elastic structure for absorbent sanitary products. The invention also relates to a method and an apparatus for producing this elastic structure.

More precisely, the invention relates to an elastic structure including a sleeve comprising two layers of non-elastic flexible material, for example nonwoven fabric, and at least one elastic thread, which extends within said sleeve and is anchored to said layers of non-elastic flexible material at connecting areas spaced apart from each other in the longitudinal direction.

Description of Prior Art

The technique generally used to produce elastic structures for diapers and the like envisages the tensioning of at least one elastic thread in the longitudinal direction within a tubular sleeve of non-elastic flexible material, and fixing the thread to the tubular sleeve at the connecting areas spaced apart in the longitudinal direction, while the elastic thread is in a tensioned state. When the thread tension is released, the tubular sleeve assumes a pleated form, with waves or folds between said connecting portions.

Elastic structures used for the edges of the openings for the legs and the leg cuffs of diapers and similar absorbent products are usually provided with elasticized portions alternating with non-elasticized portions. In the elasticized portions, the elastic threads impart the characteristic pleated forms to the flexible sleeves. The elasticized portions are located in the crotch area of the diaper. The portions of the elastic structures adjacent to the front and rear waistline usually are not elasticized to improve the fit of the article.

A traditional technique to produce elasticized structures with elastic portions alternating with non-elastic portions, in production lines of diapers, envisages the tensioning of an elastic thread in the longitudinal direction and fixing, by means of glue drops, the tensioned elastic thread to a substrate of non-elastic flexible material, for example nonwoven fabric or polyethylene. The application of the glue drops is carried out by controlled dispensing nozzles in phase with the advancing of the substrate and the elastic. The glue dispensing is interrupted to form the non-elastic portions of the structure, so that the elastic thread is not axially connected to the tubular sleeve in the non-elastic portions. In this way, when the individual articles are separated from each other with a cutting operation, the part of the structure that has the elastic thread fixed with the glue takes on the characteristic pleated form and presents characteristics of elasticity, while the part of the structure where the glue dispensing was interrupted remains smooth and non-elastically extensible since the elastic can slide freely inside it in an untensioned state.

The use of glue to anchor the elastic threads to a substrate in production lines of diapers entails considerable problems, including the difficulty of ensuring the dispensing of constant quantities of glue, the possibility of clogging of the glue dispensing apparatuses, the risk of contamination of parts of the system, and the need to carry out welding to close the elastic structures after anchoring the elastic threads.

To overcome the problems arising from the use of glue to anchor the elastic threads of an absorbent structure, anchoring of the tensioned elastic thread within a tubular sleeve by means of welding has been previously proposed. The document U.S. Pat. No. 6,291,039 describes an elastic structure comprising a tubular sleeve and at least one elastic thread, which extends inside the sleeve in a longitudinal direction. The thread is tensioned in the longitudinal direction and is anchored to the sleeve by a plurality of connecting portions spaced apart in the longitudinal direction. Each connecting portion comprises two welds that weld together opposite layers of the tubular sleeve. The two welds of each connecting portion have respective proximal surfaces facing towards the thread, spaced apart by a distance less than the diameter of the untensioned thread. When the longitudinal tensioning ceases, the thread tends to expand radially and remains anchored to the connecting portions by interference. The welds forming the connecting portions of the elastic thread are formed by a thermal or ultrasonic welding device comprising two cooperating wheels, one of which is provided on its periphery with protrusions spaced apart in the circumferential direction and provided with respective notches through which the tensioned thread is passed.

This solution, however, creates problems when elastic structures must be produced with elasticized portions alternating with non-elasticized portions. One solution used envisages the cyclical moving apart of the welding wheels in order to interrupt the welding in the non-elasticized portions. The welding wheels must be moved radially relative to each other with a high frequency, up to 1000 times per minute. A process of intermittent welding of this type generates vibrations that produce a decline in quality of the weld, particularly serious in the case of ultrasonic welding.

SUMMARY OF THE INVENTION

The present invention aims to provide an elastic structure without glue, with elasticized portions alternating with non-elasticized portions, and a method and apparatus for its production, which overcome the problems of the prior art.

According to the present invention, this object is achieved by an elastic structure, by a method and by an apparatus for its production having the characteristics forming the subject of the attached claims.

BRIEF DESCRIPTION OF THE DRAWINGS

The present invention will now be described in detail with reference to the attached drawings, given purely by way of non-limiting example, wherein.

DETAILED DESCRIPTION

Figure 1:
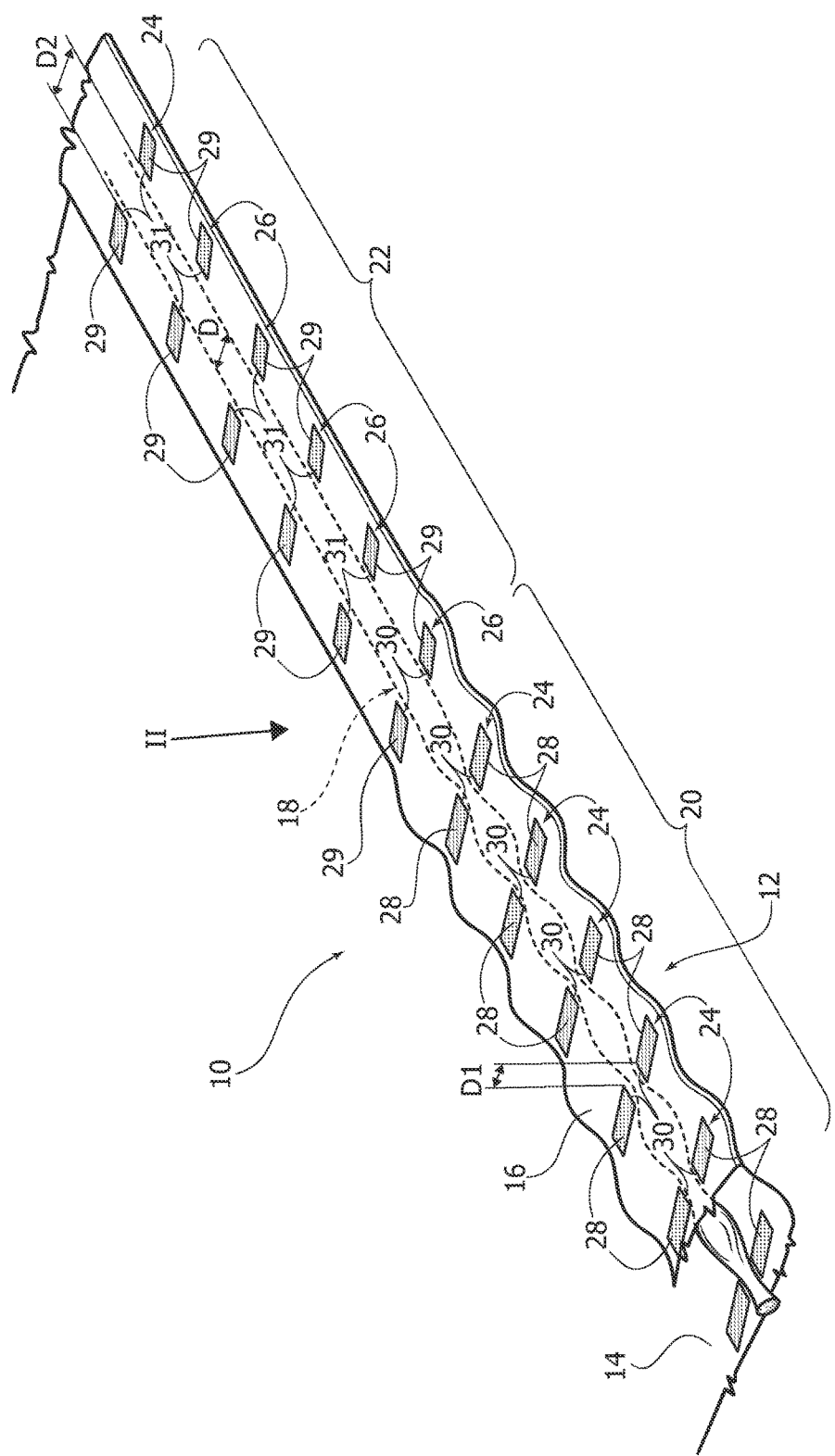
FIG. 1 is a schematic perspective view of an elastic structure without glue according to the present invention.
Figure 2:
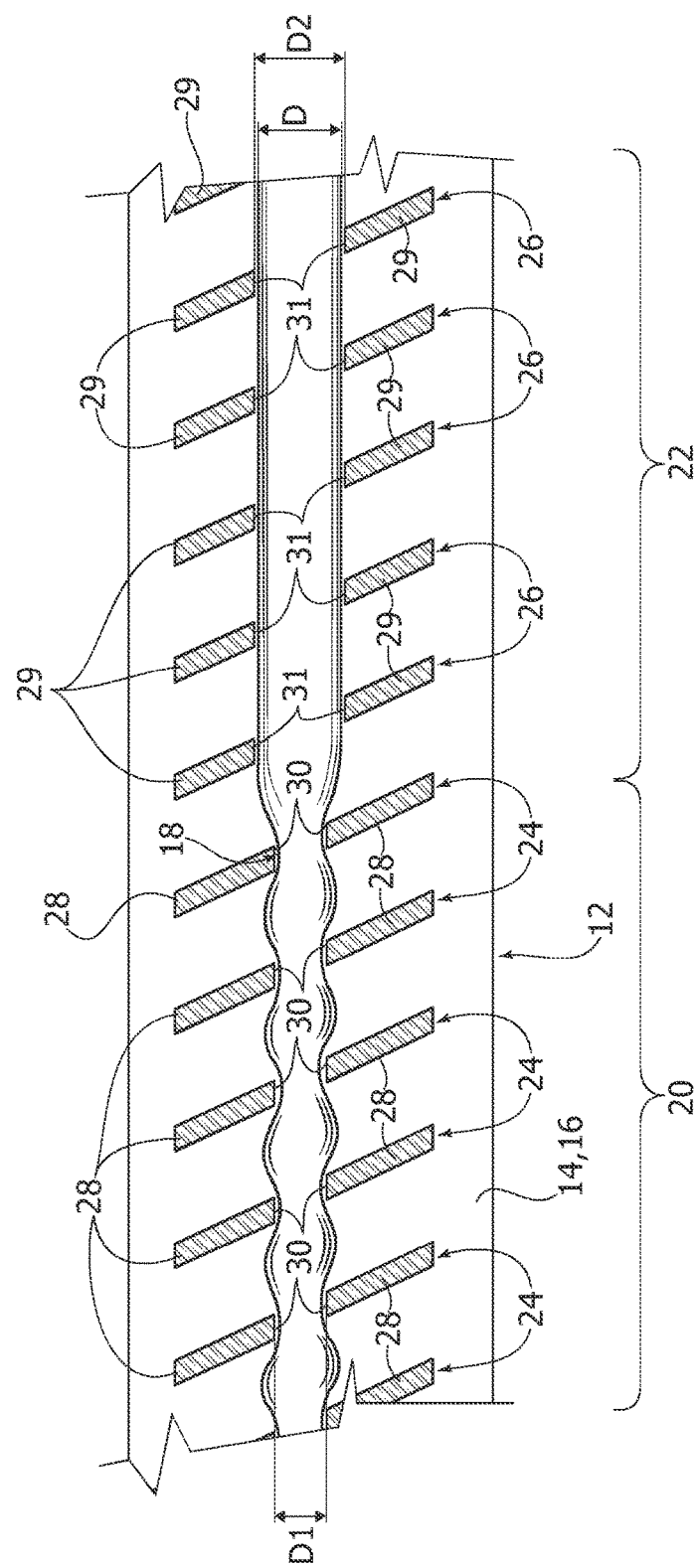
FIG. 2 is a schematic plan view according to the arrow II of FIG. 1.

In FIGS. 1 and 2, numeral 10 indicates an elastic structure 10 typically without glue with elasticized portions alternating with non-elasticized portions. The elastic structure 10 comprises a sleeve 12, which extends continuously along a longitudinal direction. The sleeve 12 comprises a first and a second layer 14, 16 overlapping each other. The second layer 16 can be a folded edge of the first layer 14, as shown in FIG. 1. Alternatively, the first and the second layers 14, 16 can be formed from two separate sheets.

The first and the second layers 14, 16 are made of non-elastic flexible material, for example nonwoven fabric. One or both layers 14, 16 forming the sleeve 12 could also be made of waterproof material, such as, for example, polyethylene.

At least one elastic thread 18 is inserted inside the sleeve 12, which extends continuously in the longitudinal direction between the two layers 14, 16. In the following description, reference will be made to only one elastic thread, but it is understood that each elastic structure may comprise two or more elastic threads. Whatever is said in relation to one thread applies in an analogous manner to the case of elastic structures with more threads. The elastic thread 18 may be monofilamentous or multifilamentous. The elastic thread 18 can be typically made of Lycra® or similar elastic materials.

The elastic structure 10 comprises first elasticized longitudinal portions 20 in which the sleeve 12 has a pleated form and second non-elasticized longitudinal portions 22 in which the sleeve 12 has a smooth form. The elasticized and non-elasticized longitudinal portions 20, 22 alternate with each other in a continuous manner in the longitudinal direction.

The thread 18 is connected to the sleeve 12 by means of a plurality of first connecting portions 24 and a plurality of second connecting portions 26. The first and the second connecting portions 24, 26 are spaced apart in the longitudinal direction. The elasticized portions 20 of the elastic structure 10 comprise a continuous array of first connecting portions 24 and the non-elasticized portions 22 comprise a continuous array of second connecting portions 26.

In the illustrated embodiment, each connecting portion 24, 26 comprises two welds 28, 29 that weld together the layers 14, 16. The welds 28, 29 of each connecting portion 24, 26 are arranged on opposite sides of the thread 18. The welds 28, 29 of each connecting portion 24, 26 have respective proximal surfaces 30, 31 facing towards the thread 18. The proximal surfaces 30 of the welds 28 of the first connecting portions 24 are spaced apart by a distance D1, less than the diameter D of the untensioned thread 18. The proximal surfaces 31 of the welds 29 of the second connecting portions 26 are spaced apart by a distance D2 greater than the diameter D of the untensioned thread 18.

Before creating the welds, 28, 29, the thread 18 is tensioned in the longitudinal direction. The longitudinal tension of the elastic thread 18 reduces the diameter of the thread 18 from a value D of the untensioned thread to a value less than the distance D1. While the thread 18 is in a tensioned state, the welds 28, 29 are created between the layers 14, 16 of the sleeve 12. After the welds 28, 29 have been made, the thread tension is released.

In the first longitudinal portions 20 of the sleeve 12 with the welds 28 of the first connecting portions 24, the thread 18 remains anchored to the first connecting portions 24. In fact, as shown schematically in FIGS. 1 and 2, after releasing the tension, the thread 18 expands in the radial direction and remains anchored between the proximal surfaces 30 of the welds 28 of the first connecting portions 24. In the second longitudinal portions 22 of the sleeve 12 at the second connecting portions 26, the thread 18 is free to expand to its resting diameter D and is not anchored to the second connecting portions 26. At the second connecting portions 26 the thread 18 is not fixed to the sleeve 12 in the longitudinal direction.

Consequently, at the first connecting portions 24, the sleeve 12 assumes a pleated form and is elastically extensible, while at the second connecting portions 26, the sleeve 12 is smooth and is not elastically extensible since the elastic thread 18 can slide freely inside the sleeve 12 regaining its untensioned status.

In an alternative embodiment, the welds 29 of the second connecting portions 26 could be on the same side of the thread 18. Each of the second connecting portions 26 may be formed by a single weld 29.

In a preferred embodiment, the welds 28 of the first connecting portions 24 and the welds 29 of the second connecting portions 26 have welding areas essentially equal to each other.

Figure 3:
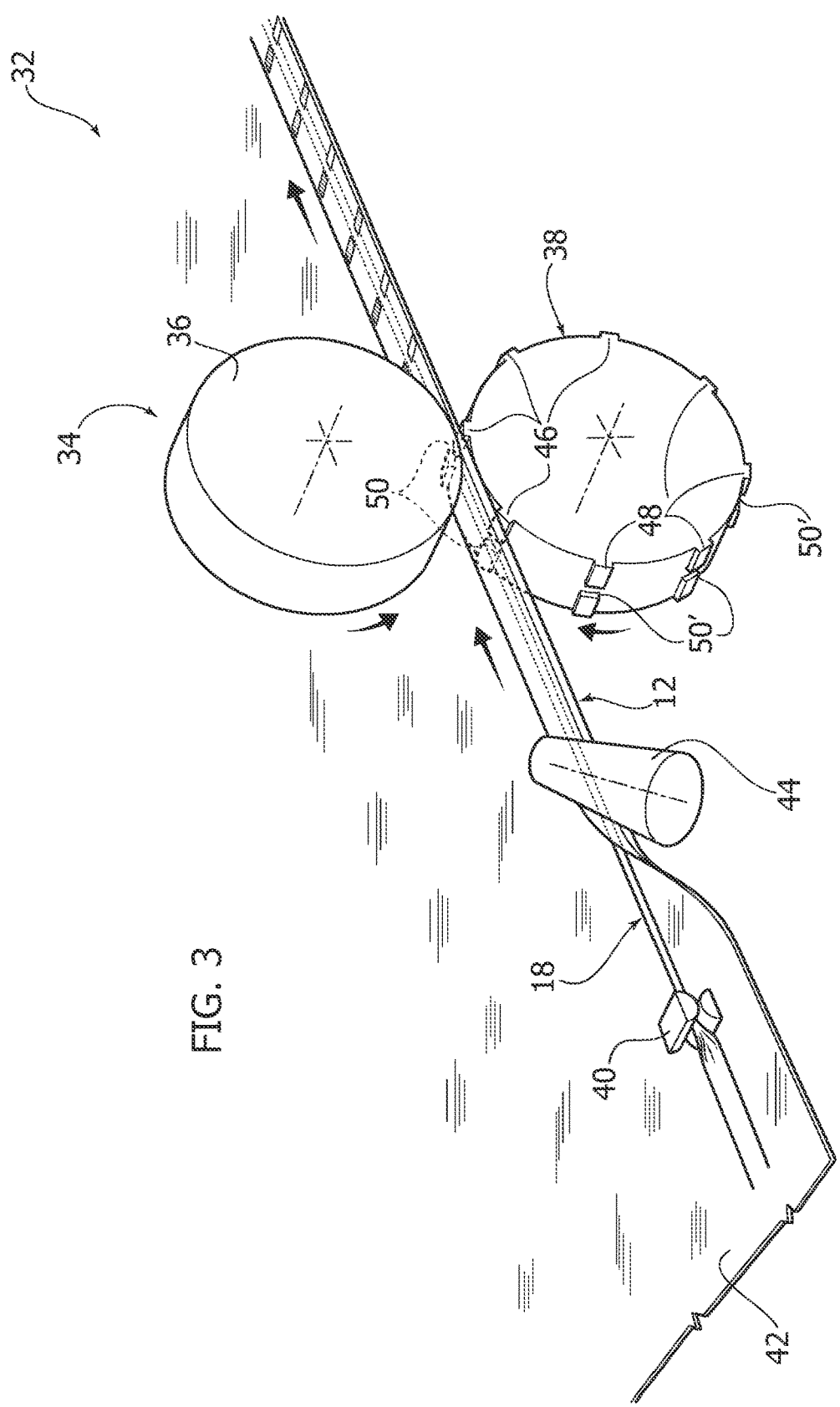
FIG. 3 is a schematic perspective view of a device for producing an elastic structure according to the present invention.

In FIG. 3, numeral 32 indicates a device for producing an elastic structure without glue according to the present invention. The device 32 comprises a welding unit 34, which comprises a welding element 36 and a welding counter-element 38.

The welding element 36 can be a thermal welding roller or, typically, the sonotrode of an ultrasonic welding device which, in turn, can be fixed or rotating with a roller-form. In the preferred embodiment illustrated in FIG. 3, the welding unit 34 is of the ultrasonic type, with the rotating sonotrode 36 cooperating with the anvil roller 38.

The elastic thread 18 is tensioned by means of a tensioning device 40 and is made to advance in a continuous manner between the two wheels 36, 38 of the welding device 34. A continuous sheet 42 is fed continuously in the longitudinal direction. A folding device, indicated schematically by 44, folds an edge of the sheet 42 and forms the sleeve 12 around the elastic 18 upstream of the welding device 34.

One of the welding wheels 36, 38 (for example, the anvil 38) has a first circumferential section with a plurality of first welding portions 46 and a second circumferential section with a plurality of second welding portions 48. The first and second welding portions 46, 48 have respective notches 50, 50' through which the tensioned thread 18—covered by the sleeve 12—is passed. The notches 50 of the first welding portions 46 have a width D1 less than the diameter D of the untensioned thread 18 and the notches 50' of the second welding portions 48 have a width D2 greater than the diameter D of the untensioned thread.

In an alternative embodiment, the second welding portions 48 may be configured to form a single line of welds only arranged on one side of the thread 18.

The wheels 36, 38 weld together the opposite layers of the sleeve 12 with welding imprints corresponding to the shape of the welding portions 46, 48. It is intended that the welding portions 46, 48 and the corresponding welds 28, 29 can have any shape, such as rectangular, trapezoidal, triangular, circular, etc.

One of the most significant aspects of the solution according to the present invention is that it is possible to obtain glue-less elastic structures with alternating elasticized and non-elasticized portions, by evenly carrying out the welding of the sleeve 12, both in the elasticized portions and in the non-elasticized portions. Thanks to the present invention, the intermittent operation of the welding unit at high frequency, which causes vibrations and overheating of the welding unit, can therefore be avoided. The constant and uniform operation of the welding unit guarantees a high quality of the weld.

Of course, without prejudice to the principle of the invention, the details of construction and the embodiments can be widely varied with respect to those described and illustrated, without thereby departing from the scope of the invention as defined by the claims that follow.

The invention claimed is:

1. An elastic structure for absorbent sanitary products, comprising
   a sleeve comprising a first layer and a second layer overlapping each other,
   at least one elastic thread which extends within said sleeve in a longitudinal direction; and
   a plurality of first connecting portions spaced apart in the longitudinal direction, wherein each of said first connecting portions comprises two first welds arranged on opposite sides of the thread, wherein the first welds weld said first layer and said second layer to each other in a first longitudinal portion of said sleeve, and wherein said first welds of each of said first connecting portions have respective proximal surfaces facing the thread spaced apart by a distance, less than the diameter of the untensioned thread, in order to anchor the thread to first said longitudinal portion of the sleeve,
   characterized in that it comprises a plurality of second connecting portions spaced apart in the longitudinal direction, wherein each of said second connecting portions comprises at least one second weld, wherein said second welds weld said first layer and said second layer to each other in a second longitudinal portion of said sleeve without axially connecting the thread to said second longitudinal portion of the sleeve.

2. An elastic structure according to claim 1, wherein each of said second connecting portions comprises two second welds arranged on opposite sides of the thread and having respective proximal surfaces facing the thread, spaced apart by a distance greater than the diameter of the untensioned thread.

3. An elastic structure according to claim 1, wherein said second welds are arranged on the same side of the thread.

4. An elastic structure according to claim 1, wherein said first connecting portions and said second connecting portions have essentially equal respective welding areas.

5. An elastic structure according to claim 1, characterized in that it is without glue.

6. A method for producing an elastic structure for absorbent sanitary products, comprising the steps of:
   tensioning a continuous elastic thread in the longitudinal direction;
   forming a continuous tubular sleeve around said elastic thread by overlapping a first and a second layer; and
   welding together said overlapping layers in a first longitudinal portion of said sleeve on opposite sides of said tensioned elastic thread, with a plurality of first connecting portions spaced apart from each other in the longitudinal direction, wherein each of said first connecting portions comprises two welds having respective proximal surfaces facing the thread, spaced apart by a distance less than the diameter of the untensioned thread,
   characterized in that it also comprises the step of welding together said overlapping layers of a second longitudinal portion of said sleeve by means of a plurality of second connecting portions spaced apart in the longitudinal direction, wherein each of said second connecting portions comprises at least one second weld, wherein said second welds weld said first and said second layers to each other without axially connecting the thread to said second longitudinal portion of the sleeve.

7. A method according to claim 6, wherein each of said second connecting portions comprises two second welds arranged on opposite sides of the thread and having respective proximal surfaces facing the thread, spaced apart by a distance greater than the diameter of the untensioned thread.

8. A method according to claim 7, wherein said second welds are arranged on the same side of the thread.

9. A method according to claim 6, wherein said first connecting portions and said second connecting portions have essentially equal respective welding areas.

10. A device for producing an elastic structure comprising:
    means for tensioning an elastic thread;
    means for forming a tubular sleeve around said tensioned thread by overlapping a first and a second layer; and
    a welding device comprising at least one welding wheel for welding together said layers of said tubular sleeve, wherein said at least one welding wheel comprises a first circumferential section with a plurality of first welding portions spaced apart in the circumferential direction, wherein each of said first welding portions is configured to form two welds on the sleeve, which are arranged on opposite parts of the thread and having respective proximal surfaces facing the thread, spaced apart by a distance less than the diameter of the untensioned thread,
    characterized in that said welding wheel comprises a second circumferential section with a plurality of second welding portions spaced apart in the circumferential direction, wherein said second welding portions are configured to form second welds on the sleeve, which weld together a second longitudinal portion of said sleeve without axially connecting the thread to said second longitudinal portion of the sleeve.

11. A device according to claim 10, wherein each of said second welding portions is configured to form two welds arranged on opposite sides of the thread and having respective proximal surfaces facing the thread, spaced apart by a distance greater than the diameter of the untensioned thread.

12. A device according to claim 10, wherein said second welding portions are configured to form second welds arranged on the same side of the thread.

13. A device according to claim 10, wherein said first welding portions and said second welding portions are configured to form welds having essentially equal respective welding areas.

* * * * *